United States Patent [19]
Pettit

[11] Patent Number: 5,554,725
[45] Date of Patent: Sep. 10, 1996

[54] SYNTHESIS OF DOLASTATIN 15

[75] Inventor: George R. Pettit, Paradise Valley, Ariz.

[73] Assignee: Arizona Board of Regents acting on behalf of Arizona State University, Tempe, Ariz.

[21] Appl. No.: 306,146

[22] Filed: Sep. 14, 1994

[51] Int. Cl.$^6$ .............................. C07K 5/00; C07K 7/00; C07K 17/00
[52] U.S. Cl. .................... 530/330; 530/329; 530/333
[58] Field of Search ................................ 530/330, 329, 530/303

[56] References Cited

PUBLICATIONS

Pettit et al. J. Am. Chem. Soc. vol. 113. p. 6692 (1991).

Primary Examiner—Toni R. Scheiner
Assistant Examiner—Sheela J. Huff
Attorney, Agent, or Firm—Richard R. Mybeck

[57] ABSTRACT

The present invention relates to the synthesis of natural (−)-dolastatin 15 and the elucidation of the absolute configuration of this important sea hare constituent. A segment synthetic strategy was utilized for obtaining the Dolabella auricularia (Indian Ocean sea hare) depsipeptide dolastatin 15. Reaction of protected (S)-Hiva-(S)-Phe (2c) with isopropenyl chloroformate followed by Meldrum's ester, cyclization (2c→3a) of the product in toluene and finally methylation afforded the key (S)-dolapyrrolidine (Dpy) derivative (3b). Condensation of tripeptide (8) with the three unit Dpy segment (5b) followed by deprotection and coupling (diethyl phosphorocyanidate) led to dolastatin 15 in 11% overall yield. The powerful and selective activity of dolastatin 15 against the U.S. National Cancer Institute's panel of human cell lines is reported.

19 Claims, No Drawings

SYNTHESIS OF DOLASTATIN 15

INTRODUCTION

The present invention relates generally to a new and useful synthesis of the depsipeptide dolastatin 15 employing a segment synthetic strategy. Ever since dolastatin 15 was first extracted from the *Dolabella auricularia* (Indian Ocean sea hare), isolated, and found to possess cell growth inhibitory properties, the synthesis of this unique substance has presented a major challenge. The present invention represents a significant step forward in obtaining this important substance in commercially viable quantities.

The work described herein was funded in part by N. I. H. Outstanding Investigator Grant CA44344-01-05. The United States government may have certain rights to the invention.

BACKGROUND OF THE INVENTION

The rapidly intensifying search for biologically and medicinally important marine organism constituents has attracted a great deal of interest world-wide. Not unexpectedly, a reassuring number of marine animals, plants and microorganisms are being found to produce promising anticancer substances of unprecedented structural types.

Discovery and synthesis of potentially useful antineoplastic peptides from naturally occurring materials comprises one of the most essential and promising approaches for new anticancer drugs. Of special interest at the Cancer Research Institute of Arizona State University, Tempe, Ariz., are the dolastatins, an unprecedented series of structurally separate linear and cyclic antineoplastic and/or cytostatic peptides which are isolated from the Indian Ocean sea hare *Dolabella auricularia*. Presently dolastatin 10 and dolastatin 15 represent the two most potent, and hence most important, members of those isolates. While dolastatin 10 has recently yielded to total synthesis (See: U.S. Pat. No. 4,978,744, Pettit et al, Dec. 18, 1990), the corollary problem of devising a total synthesis of dolastatin 15 remained a challenge.

The need for such a total synthesis was further dramatized when a determination of the vast number of *Dolabella auricularia* that would have to be harvested in order to provide sufficient dolastatin 15 to meet the projected public need was made. Thus, without an economically viable method of synthesis, dolastatin 15 could be effectively barred from consideration for human therapy because of the astronomical investment required for commercial production. The natural substance must be tightly replicated from lot to lot because the entrainment of even a slight amount of unidentifiable impurities in the extracted product could create problems which would prevent the natural substance from meeting the strict uniformity required for the approval by the United States Food, Drug and Cosmetic Administration (FDA) and corresponding regulatory agencies of other nations.

Accordingly, an important need exists for the development of an economically viable and truly replicable procedure for synthetically producing substantially pure dolastatin 15 in sufficient quantities to meet the public demand. It is toward the fulfillment of that need that the present invention is directed.

BRIEF SUMMARY OF THE INVENTION

The present invention relates to the synthesis of dolastatin 15 by reacting t-Butyldimethylsilyl-(S)-Hiva-(S)-Phe (2c) with isopropenyl chloroformate followed by Meldrum's ester (See: Jouin et al., *J. Chem. Soc*, Perkin Trans. I., 1987, 1177–1182) and the cyclization (2c→3a) of that product in toluene and finally methylation to produce the key (S)-dolapyrrolidine (Dpy) derivative (3b). Condensation of tripeptide (8) with the three unit Dpy segment (5b) followed by deprotection and coupling (diethyl phosphorocyanidate) led to dolastatin 15 in 11% overall yield. The powerful and selective activity of dolastatin 15 against the U.S. National Cancer Institute's panel of human cell lines has been summarized.

The resulting product has the structure shown below:

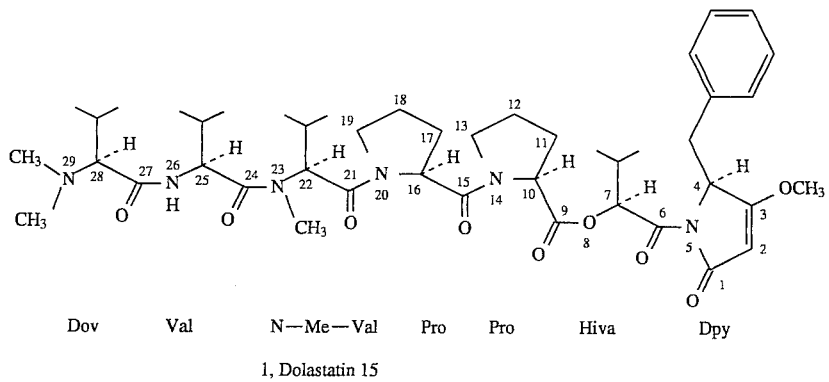

1, Dolastatin 15

Accordingly, a principle object of the present invention is to provide a reliable and economically viable method of synthesizing natural dolastatin 15.

A further object of the present invention is to provide a process for synthesizing dolastatin 15 which can be readily duplicated to provide a continual and uniform product supply.

These and still further objects as shall hereinafter appear are readily fulfilled by the present invention in a remarkably unexpected manner as will be readily discerned from the following detailed description of an exemplary embodiment thereof.

DESCRIPTION OF PREFERRED EMBODIMENT

The structure of dolastatin 15, elucidated using extensive 2D NMR and high resolution mass spectral techniques, was found to contain a new pyrrolidone amino acid designated dolapyrrolidone (Dpy), as well as 2-hydroxy-isovaleric acid (Hiva), dolavaline (Dov), proline, valine, and N-methylvaline units. While the paucity of natural product prevented the determination of the absolute configuration of natural (−)- dolastatin 15 from that source, it was assumed that the dolastatin 15 amino acids most probably possessed the common L-configuration (S used in the sequel) previously found in dolastatin 10. The present synthesis of dolastatin 15 is predicated on that premise.

Dolastatin 15 has been found to strongly and selectively inhibit (TGI<$10^{-9}$ μg/mL) the growth of thirteen human cancer cell lines included in the U.S. National Cancer Institute human cell line panel. (See: Bai et al., *J. Biol. Chem*, 1991, 266, 15882). Originally 6.2 mg ($4 \times 10^{-7}\%$ yield) of dolastatin 15 was isolated from 1,600 kg (wet wt.) of the sea hare. Since dolastatin 15 has been selected for eventual clinical trial, a practical total synthesis was urgently required. In 1989, the first total synthesis of this promising new depsipeptide was completed, but further work led to the conclusion that it was not commercially viable. The present invention is predicated upon a new and novel synthetic route which results in a very practical method for preparing natural (−)-dolastatin 15 in quantity.

Structurally, dolastatin 15 is derived from (S)-dolapyrrolidone (Dpy), (S)-2-hydroxy-isovaleric acid (Hiva), dolavaline (Dov), two units of proline, valine, and N-methylvaline. Dolapyrrolidone (2) falls in a class of modified amino acids presumably derived biosynthetically from phenylalanine through a two carbon condensation. Natural products containing a glycine derived pyrrolidone C-terminus have previously been found in Streptomyces (e.g. the antibiotic althiomycin), the blue green algae components malyngamide, and pukeleimide. Dysidin, a constituent of both sponges and blue green algae, contains a valine derived pyrrolidone C-terminus. Very recently a hexachloro metabolite, dysidamide, was isolated from a Dysidea species of sponge. Hiva is found to be incorporated in the Hip unit of the potent tunicate didemnins.

In order to start the original synthesis in an orderly fashion, it was assumed that all of these amino acids have possessed the L (S)-stereochemistry previously found in dolastatin 10. The challenge of realizing racemizaton-free coupling of Dpy with Hiva was apparent due to the non-nucleophilic nature of the Dpy nitrogen. In order to avoid the total racemization which was encountered in preliminary experiments involving generation of the nitrogen anion with sodium hydride in tetrahydrofuran, it was decided to synthesize (S)-Hiva-(S)-Phe-OMe (2a) and conduct a ring closure of the protected derivative (2c) to afford a blocked Hiva-Dpy (3a). In turn (S)-Hiva was prepared from (S)-valine through a well known, (See: Kim et al., *J. Org. Chem.* 1987, 52,4531; and Cook et al., *J. Chem. Soc*, 1949, 1022) diazotation procedure with retention of configuration. The (S)-Hiva was coupled with Phe-OMe hydrochloride using diethyl phosphorocyanidate (DEPC) in the presence of N-methylmorpholine to give (S)-Hiva-(S)-Phe-OMe (2a). The Hiva-Phe-OMe was further protected (with excellent yield) using t-butyldimethylsilyl chloride in the presence of imidazole using the technique of Corey et al. (See: *J. Am. Chem. Soc.*, 1972, 94, 6190, 4475). Cleavage (2b→2c) of the methyl ester was performed using mild alkaline conditions.

Dolapyrrolidone derivative (3a) was synthesized via acylation of Meldrum's ester as per Oikawa et al., (*J. Org. Chem.* 1978, 43, 2087). Isopropenyl chloroformate was found to give the best results of several mixed carbonic anhydrides derived from carboxylic acid (2c), when used in the presence of five molar equivalents of 4-dimethylaminopyridine. After removal of base using 10% aqueous $KHSO_4$ the Meldrum's ester adduct was heated in refluxing toluene to afford pyrrolidone (3a) in 68% yield. Methylation of the tautomeric mixture (3a) using dimethylsulfate and potassium carbonate in tetrahydrofuran gave methyl vinyl ether (3b), without any detectable C-alkylated product. Some racemization was detected at the Phe center to give an approximate product ratio of 7.4:1 S,S: S,R TBDMS-Hiva-Dpy (3b). The S,R isomer side-product was easily removed using a column chromatographic separation. The yield of pyrrolidone (3a) fell dramatically to 21% and lower when the Meldrum's ester adduct was cyclized in methanol which was believed to be caused by simple keto ester formation.

Currently a variety of reagents are available for removal of silyl groups. Earlier successful (90% yield) cleavage of the silyl ether (3b) using pyridinium polyhydrogen fluoride was obtained (See: Pettit et al. *J. Am. Chem. Sec.* 1991, 113, 6692). Later, the use of trifluroacetic acid was discovered to lead to quantitative yields. In contrast, tetrabutylammonium fluoride in tetrahydrofuran solution gave only poor results. Esterification of alcohol (4) with Boc-(S)-Pro using dicyclohexylcarbodiimide (DCCI) with 4-pyrrolidinopyridine gave the desired depsipeptide (5a) in 92% yield. Depsipeptide (5a) was shown by X-ray crystal structure determination to have the chirality required for conversion to dolastatin 15. Removal of the Boc-protecting group was accomplished in quantitative yield using trifluoroacetic acid to provide amine (5b).

Since proline coupling is usually racemization free, a segment condensation approach based on coupling at Pro was adopted for completing the synthesis of dolastatin 15. Consistently higher yields were obtained by coupling the two tripeptide units (8) and (5b) followed by final condensation with Dov, rather than coupling the tetrapeptide (Dov-(S)-Val-Nme-(S)-Val-(S)-Pro) with the depsipeptide (bb) at the Pro-Pro linkage. Condensation of N-Z,N-Me-(S)-Val with (S)-Pro-OMe was obtained employing the DEPC coupling procedure to give dipeptide (6) in 77% yield. Cleavage of the carbobenzoxy protecting group by hydrogenolysis was followed by coupling with the mixed anhydride prepared from pivaloyl chloride and Z-(S)-Val to afford (83%) tripeptide (7). The pivaloyl anhydride procedure was previously employed in our dolastatin 10 synthesis at an analogous location involving coupling of an N-Me-amino acid. A similar step appears in synthesis of the immunosuppressive peptide cyclosporine.

The methyl ester group of tripeptide (7) was removed using dilute base and the resulting carboxylic acid (8) was coupled with depsipeptide (5b) using DEPC to give Z-protected depsipeptide (9a). Deprotection by hydrogenolysis yielded the corresponding amine (9b) which was then coupled (DEPC) with dimethyl valine (Dov). Dolastatin 15 (1) was obtained in 97% yield by SILICA GEL column chromatographic purification. Final purification by recrystallization gave finely divided colorless crystals identical with natural (−)-dolastatin 15 (1). Identity was confirmed by results of high field (400 MHz) $^1$H-NMR, $^{13}$C-NMR, and mass spectral comparison combined with biological, detailed high performance liquid (and thin layer) chromatographic, and optical rotation results.

Dolastatin 15 (1) was found to strongly inhibit progression of an important series of human cancer cell lines among the U.S. National Cancer Institute's disease oriented panel. Remarkable potency (TGI $\log_{10}$ −7 to −9) and selectivity was exhibited against non-small cell lung (NCI-H23), NCI-H552), small cell lung (DMS-114, DMS-273), colon (COLO-205, HCC2998, HT29, KM-20L2), brain (SF-295, SF-539), melanoma (SK-MEL-2, SK-MEL-5), ovary (OVCAR-3), renal (SN12K1) cancers and a leukemia (HL-60TB). A number of human cancer xenograft studies and other preclinical research objectives are currently in progress.

EXPERIMENTAL SECTION

The amino acids and derivatives S-phenylalanine methyl ester hydrochloride, S-proline methyl ester hydrochloride, N-Boc-(S)-proline, S-valine, and Z-S-valine, were employed as obtained from Sigma-Aldrich Co. Other reagents were also obtained from Sigma-Aldrich or Lancaster Synthesis. Solvents were redistilled and solvent extracts of aqueous solutions, unless otherwise noted, were dried, over anhydrous magnesium sulfate. Evaporation of solvents was performed under reduced pressure on a Buchi rotary evaporator. Ether refers to diethyl ether, THF to tetrahydrofuran, DMF to dimethylformamide, DME to ethylene glycol dimethyl ether and EtOAc to ethyl acetate. The THF was distilled from lithium aluminum hydride prior to use.

ANALTECH SILICA GEL GF (0.25 mm) plates were used for thin layer chromatography (TLC) and high performance thin layer chromatography (HPTLC) and developed with either 3% ceric sulfate in 3N sulfuric acid spray and/or iodine vapor. Stationary phases used for gravity or flash column chromatography were E. MERCK (Darmstadt) SILICA GEL (70–230 mesh; for gravity column and 40–63 for flash column).

Melting points were observed with an ELECTROTHERMAL digital-melting-point apparatus, model IA9200. Optical rotation measurements were recorded using a PERKIN-ELMER 241 polarimeter. The ultraviolet spectra were obtained in methanol solution with a HEWLETT-PACKARD 8450A UV/vis spectrophotometer. A MATTSON 2020 GALAXY FT spectrophotometer was employed for infrared measurements. Tetramethylsilane, residual chloroform (7.256 ppm) or dichloromethane (5.32 ppm) was used as an internal reference in all nuclear magnetic resonance measurements determined with BRUKER AM 400 ($^1$H, $^{13}$C) or VARIAN AM 300 Gemini instruments. Chemical shifts were recorded in ppm and peak multiplicities not designated in full are thus: s, singlet; d, doublet; t, triplet; dd, double-doublet; dt, double-triplet; bd, broad-doublet; m, multiplet. Deuteriochloroform was used as the NMR solvent unless otherwise mentioned. The HREI and SP-SIMS (FAB) mass spectra were recorded with a KRATOS MS 50 instrument in the NSF regional mass spectrometry facility at the University of Nebraska.

The HPLC analyses were performed using a reverse phase PHENOMENEX ULTREMEX 3 $C_8$ column (100×4.6 mm) and an analytical GILSON HPLC (802B, 811, 2×302), equipped with a RHEODYNE injection valve (7125 with a 20 µl loop), working pressure ~94– 101 bar. Control of the HPLC was performed with an APPLE IIe gradient manager (V 1.2 GILSON). Detection was accomplished with a UV detector (UV detection at 230 nm, range 210–400 nm) contained within a diode-array data station (HEWLETT-PACKARD 1040A, 9000-300, 9153). Chromatographic spectra and data analyses were plotted with a HEWLETT-PACKARD COLORPRO plotter. Elemental analyses were determined by Dr. A. W. Spang (Spang Microanalytical Laboratory, Eagle Harbor, Mich.).

(S)-Hiva-(S)-Phe-OMe (2a).

To a stirred and cooled (0° C.) solution composed of (S-2-hydroxy-isovaleric acid (5 g, 42.3 mmol), (S)-phenylalanine methyl ester hydrochloride (9.12 g, 42.3 mmol), and 4-methylmorpholine (9.3 mL, 84.6 mmol) in dry $CH_2Cl_2$ (100 mL) was added diethyl phosphorocyanidate (6.4 mL, 42.3 mmol). After 2 hours, the solution was washed with water (100 mL), dried ($Na_2SO_4$) and concentrated under reduced pressure. The oily residue was dissolved in $CH_2Cl_2$ (5 mL) and placed on a column of SILICA GEL (4×37 cm) and eluted with 1:4 EtOAc-$CH_2Cl_2$. The appropriate fractions were combined and concentrated under reduced pressure to give an oil 7.17 g (61%). An aliquot was recrystalized (3X) from toluene-hexane to give colorless needles: mp 73° C.; $[\alpha]^{23}D=-24°$ (c=0.2, $CHCl_3$); EIMS (m/z); 279 (3.4, M$^+$); 178 (6.8, M$^+$-Hiva); 120 (79); 88 (100%); NMR (300 MHz) δ0.74 (d, J=7.0 Hz, 3H, Val $CH_3$), 0.97 (d, J=7.0 Hz, 3H, Val $CH_3$), 2.08 (m, 1H, Val CH β), 2.66. (bd, J=5.1, 1 Hz, 1H, OH), 3.12 (m, 2H, phenyl $CH_2$), 3.73 (s, 3H, $OCH_3$), 3.95 (m, 1H, Val CH α), 4.92 (m, 1H, Phe CH α), 6.85 (bd, J=7.9 Hz, 1H, amide NH), 7.15 (m, 2H, 2 × phenyl H), 7.29 (m, 3H, 3 × phenyl H).

Anal. Calcd for $C_{15}H_{21}NO_4$: C, 64.49; H, 7.58; N, 5.01. Found: C, 64,62; H, 7.71; N, 5.14.

O-t-Butyldimethylsilyl-(S)-Hiva-(S)-Phe-OMe (2b)

To a stirred solution of (S)-Hiva-(S)-Phe-OMe (2a), 2.79 g, 10 mmol) and imidazole (2.03 g, 30 mmol in dry DMF (30 mL) was added t-butyldimethylsilyl chloride (2.26 g, 15 mmol). After 18 hours in the absence of moisture at 40° C., ether (200 mL) was added. The solution was washed with water (2–100 mL), dried and concentrated to an oil. The residual oil was dissolved in $CH_2Cl_2$ (5 mL) and applied to a column of silica and fractions eluted with $CH_2Cl_2$. The appropriate fractions were combined and concentrated to give a clear oil (3.42 g, 87%): $[\alpha]^{24}{}_D$ –40° (C=0.2, $CHCl_3$); NMR (300 MHz) δ0.02 (s, 3H, $SiCH_3$), 0.06 (s, 3H, $SiCH_3$), 0.74 (d, J=6.9 Hz, 1H, Val $CH_3$), 0.87 (s, 9H, t-Bu), 0.89 (d, J=6.9 Hz, 3H, Val $CH_3$), 2.05 (m, 1H, Val CHα), 3.10 (m, 2H, $CH_2$), 3.70 (s, 3H, $OCH_3$),3.93 (d, J=3.3 Hz, 1H, Val CHα), 4.96 (m, 1H, Phe CHα), 6.92 (bd, J=8.5 Hz, 1H, amide NH), 7.14 (m, 2H, 2 × phenyl H) , 7.27 (m, 3H, 3 × phenyl H); MS m/z 393 (0.7, M$^+$), 378 (1.4, M$^+$—$CH_3$), 362 (0.5, M$^+$—$CH_3$)2), 336 ( 100, M$^+$-t-Bu)%. Anal. Calcd for $C_{21}H_{35}NO_4Si$: C, 64.08; H, 8.96; N, 3.56. Found: C, 63.82; H, 8.77; N, 3.75.

t-Butyldimethylsilyl-(S)-Hiva-(S)-Phe (2c)

To a vigorously stirred solution of t-butyldimethylsilyl-(S)-Hiva-(S)-Phe-OMe (2b, 3.58 g, 9.1 retool) in EtOH (20 mL) and water (40 mL) was added sodium hydroxide solution (1.0 N, 18.4 mL, 18.4 mmol). Saponification was conducted at room temperature for 30 minutes and the clear solution was acidified to pH 3.0 using saturated citric acid solution. The product was extracted with ethyl ether (2×50 mL) and the fractions combined, dried, and concentrated to give a solid (3.1 g, ) Recrystallization from hexane led 90% . to pure colorless crystals: mp 87°–88° C.; $[\alpha]^{24}{}_D$ –18° (c=0.2, $CHCl_3$); MS m/z 379 (0.7, M$^+$), 364 (2, M$^+$—$CH_3$), 335 (M$^+$—$CO_2$), 322 (100, M$^+$-t-Bu)%. $^1$H-NMR (300 MHz) δ0.04 (s, 6H, 2× $SiCH_3$), 070 (d, J=6.8 Hz,3H, Val $CH_3$), 0.85 (s, 9H, t-Bu), 0.86 (d, J=6.8 Hz, 3H, Val $CH_3$), 2.00 (m, 1H, Val CHβ), 3.16 (m, 2H, $CH_2$), 3.97 (d, J=3.2 Hz, 1H, Val CHα) , 4.94 (m, 1H, Phe CHα), 6.94 (bd, J=8.6 Hz, 1H, amide NH), 7.18–7.33 (m, 5H,phenyl), carboxylic acid not seen.

Anal. Calcd for $C_{20}H_{33}NO_4Si$: C, 63.29; H, 8.76; N, 3.69. Found: C, 63.54; H, 9.28; N, 3.89.

O-t-Butyldimethylsilyl-(S)-Hiva-(S)-Dpy (3b)

To a stirred and cooled (−10° C.) solution of t-butyldimethylsilyl-(S)-Hiva-(S)-Phe (2c, 7.6 g, 20 mmol) in dry CH$_2$Cl$_2$ (10 mL) was added 4-dimethylaminopyridine (12.2 g, 0.1 mmol) and Meldrum's ester (3.18 g, 22 mmol). The solution was stirred in the absence of moisture for 2 hours at −10° C., and then allowed to rise to 0° C. and stirred for an additional 2 hours. The reaction mixture was then washed with 10% aqueous NaHSO$_4$ solution (2×200 mL), followed by water (100 mL), dried and concentrated to an oil. The oil was dissolved in toluene (150 mL) and the solution heated at reflux for 1 hour. Concentration under reduced pressure gave a pale reddish oil which was dissolved in dry THF (150 mL). To this solution was added potassium carbonate (8 g, 58 mmol) and dimethyl sulfate (5 mL, 50 mmol). The mixture was stirred for 18 hours and the solution filtered through a bed of celite. Concentration (in vacuo) gave an oil which was dissolved in CH$_2$Cl$_2$ (10 mL) and placed on a column of silica gel. The chromatography column was eluted with CH$_2$Cl$_2$ to give firstly t-butyldimethylsilyl-(S)-Hiva-(R)-Dpy, a clear oil which later crystallized (0.74 g, 9.2%) followed by the optically pure S,S-product (2c), a clear oil (5.45 g, 68%) which soon crystallized: mp 110°–111° C.; $[\alpha]^{24}_D$ +165° (c=0.2, CHCl$_3$); MS m/z 417 (2,M$^+$), 402 (3.6, M$^+$—CH$_3$), 360 (100, M$^+$-t-butyl)%; $^1$H-NMR (300 MHZ) δ0.10 (s, 3H, SiCH$_3$), 0.84 (d, J=6.9 Hz, 3H, Val CH$_3$), 0.98 (s, 9H, t-Bu), 1.00 (d, J=6.9 Hz, 3H, Val CH$_3$), 1.97 (m, 1H, Val CH β), 3.19 (dd, J=3.0, 13.8 Hz, 0.5 Phe CH$_2$), 3,62 (dd, J=5.3, 13.8 Hz, 0.5 CH$_2$), 3.80 (s, 3H, OCH$_3$), 4.76 (dd, J=3.0, 5.3 Hz,H-5), 4.81 (s, 1H,H-3), 5.28 d, J=2.8 Hz, 1H, Val CH), 7.04 (m, 2H, 2 × phenyl H), 7.21 (m, 3H, 3 × phenyl H).

Anal. Calcd for C$_{23}$H$_{35}$NO$_4$Si: C, 66.15; H, 8.45; N, 3.35. Found: C, 66.61; H, 8.85; N, 3.42.

(S)-Hiva-(S)-Dpy (4)

Trifluoroacetic acid (15 mL) was added to a stirred solution of t-butyldimethylsilyl-(S)-Hiva-(S)-Dpy (3b), 2.59 g, 6.2 mmol) in CH$_2$Cl$_2$ (200 mL). After 2 hours the solvent was removed under reduced pressure. The oily residue was dissolved in CH$_2$Cl$_2$ (10 mL) and chromatographed on a column of SILICA GEL. Elution with CH$_2$Cl$_2$-EtOAc (10:1) led to the alcohol as a clear oil (1.88 g, 100%): $[\alpha]^{23}_D$ +285° (c=0.2, CHCl$_3$); MS m/z 303 (0.7%, M$^+$); $^1$H-NMR (300 MHz) δ0.87 (d, J=6.9 Hz, 3H, Val CH$_3$), 1.08 (d, J=6.9 Hz, 3H, Val CH$_3$), 2.13 (m, 1H, Val CH β), 3.13 (dd, J=2.8, 13.9 Hz, 0.5 Phe CH$_2$), 3.65 (dd, J=5.0, 13.9 Hz, 0.5 Phe CH$_2$), 3.66 (br, 1H, OCH$_3$) , 4.79 (m, 1H, H-5), 4.83 (s, 1H, H-3), 4.85 (d, J=2.9 Hz, 1H, Val CHα), 6.97 (m, 2H, 2 × phenyl), 7.24 (m, 3H, 3 × phenyl).

Anal. Calcd for C$_{17}$H$_{21}$NO$_4$: C, 67.31; H, 6.97; N, 4.61. Found: C, 67.39; H, 7.06; N, 4.65.

Boc-(S)-Pro-(S)-Hiva-(S)-Dpy (5a)

A solution of Boc-(S)-proline (2.13 g, 9.89 mmol), (S)-Hiva-(S)-Dpy (4), 2.52 g, 8.29 mmol), DCCI (2.04 g, 9.89 mmol), and 4-pyrrolidinopyridine (1.47 g, 8.29 retool) in CH$_2$Cl$_2$ (25 mL) was stirred at room temperature under an argon atmosphere overnight. The precipitated dicyclohexylurea was removed by filtration and the filtrate concentrated under reduced pressure to give a yellow oil. A solution of the oil in CH$_2$Cl$_2$ (10 mL) was added to a SILICA GEL column and elution performed with CH$_2$Cl$_2$-EtOAc (10:1). The appropriate fractions were concentrated to give a crystalline solid (3.83 g, 92%). Recrystallization from toluene-hexane afforded analytically pure crystals: mp 157°–158° C.; $[\alpha]^{30}_D$ +96° (c=0.19, CHCl$_3$); EIMS (m/z: 500 (5, M$^+$), 444 (7), 399 (12), 286 (10), 240 (8), 204 (15), 170 (24), 114 (100)%; IR (NaCl) V$_{MAX}$ 1749, 1729, 1699, 1629, 1394, 1380, 1367, 1308, 1196, 1168 cm$^{-1}$, $^1$H-NMR (300 MHz) two conformers in the ratio of 3:1 δ0.90 (d, J=6.9 Hz, 3H, Val CH$_3$), 1.04 (d, J=6.9 Hz, 3H, Val CH$_3$), 1.42, 1.44 (s, 9H, t-Bu), 1.91 (m, 2H, Pro CH$_2$), 2.25 (m, 1H, CHβ), 2.25 (m, 2H, Pro CH$_2$) , 3.06 (dd, J=3.3, 13.9 Hz, 1H, 0.5 Phe CH$_2$), 3.55 (dd, J=5.0, 13.9 Hz, 1H, 0.5 Phe CH$_2$), 3.59 (m, 1H, 0.5 Pro CH$_2$), 3.71, 3.74 (s, 1H, OCH$_3$), 4.36, 4.49 (t, J=6.1 Hz, 1H, CHα), 4.69, 4.71 (s, 1H, H-3), 4.76 dd, J=3.0, 5.0 Hz, 1H, H-5), 5.83, 5.89 (d, J=2.5 Hz, Hiva CHα), 7.08 (m, 2H, phenyl H), 7.18 (m, 3H, phenyl H); $^{13}$C-NMR (400 MHz) 15.83 (Hiva-CH$_3$), 23.46 (Pro-CH$_2$), 28.31 (t-Bu CH$_3$), 28.52 (Pro-CH$_2$), 30.75 (Hiva-CH), 34.94 (Dpy-CH), 46.34 (Pro-CH2), 58.36 (Dpy-CH), 58.72 (Pro-CH), 60.02 (Dpy-OCH$_3$), 77.68 (Hiva-CH), 79.93 (Pro-CO), 94.72 (Dpy-CH), 127.02 (Dpy-CH), 128.24 (Dpy-2 × CH), 129.92 (Dpy-2 × CH), 133.98 (Dpy-C-1), 154.02 (Pro-CO) 169.14 (Pro-CO), 169.57 (Hiva-CO), 172.64 (Dpy-CO), 178.42 (Dpy-CO).

Anal. Calcd for C$_{27}$H$_{36}$N$_2$O$_7$: C, 64.78; H, 7.25; N, 5.60. Found: C, 64.90; H, 7.34; N, 5.63.

(S)-Pro-(S)-Hiva-(S)-Dpy (5b). To a cool (ice-bath) and stirred solution of the depsipeptide (5b, 1.48 g, 2.96 mmol) in CH$_2$Cl$_2$ (100 mL) was added trifluroacetic acid. One hour later the solvent was removed under reduced pressure, toluene (25 mL) was added and the solution was reconcentrated, under reduced pressure, to give a clear oil. The oil was dissolved in CH$_2$Cl$_2$ (25 mL) , the solution cooled to 0 ° C., triethylamine (5 mL) added, and the mixture stirred for five minutes. The solution was then concentrated and the resulting oil dissolved in CH$_2$Cl$_2$ and added to a column of SILICA GEL. The product was eluted with 5% EtOH in CH$_2$Cl$_2$. The analogous fractions were combined and concentrated to give a clear gum/glass (1.19 g, 100%): $[\alpha]^{23}_D$ +136° (C=0.28, CHCl$_3$); EIMS (m/z) 400 (2.8, M$^+$), 356 (12), 302 (3.2, M$^+$-Pro), 287 (302—CH$_3$)%; $^1$H-NMR (300 MHz) δ0.94 (d, J=7.0 Hz, 3H, Val CH$_3$), 1,09 (d, J=7.0 Hz, 3H, Val CH$_3$), 1.94 (m, 1H, Pro CH$_2$), 2.27 (m, 1H, Val CHβ), 2.37 (m, 2H, Pro CH$_2$), 3.07 (dd, J=14.0, 3.5 Hz, 1H, 0.5 Phe CH$_2$), 3.24 (m, 2H, Pro CH$_2$), 3.57 (dd, J = 14.0, 4.4 Hz, 1H, 0.5 Phe CH$_2$), 3.79 (s, 3H, OCH$_3$), 4.33 (t, J=6.9 Hz, 1H, Pro CHα), 4.76 (s, 1H, H-3), 4.79 (m, 1H, Phe H-5), 5.93 (d, J=2.6 Hz, 1H, Val CHα), 7.10 (m, 2H, 2 × phenyl), 7.24 (m, 3H, 3 × phenyl); $^{13}$C-NMR (400 MHz): 15.77, 19.74, 25.16, 28.83, 30.08, 34.85, 46,886, 58.31, 59.43, 59.92, 77.78, 94.69, 126.97, 128.15, 129.84, 133.96, 169.13, 169.43, 174.90, 178.32.

Anal. Calcd for C$_{22}$H$_{28}$N$_2$O$_5$: C, 65.98; H, 7.05; N, 7.00. Found: C, 64.45; H, 7.17; N, 7.57.

Z-NMe-(S)-Val-(S)-Pro-OMe (6)

A stirred solution of (S)-proline methyl ester hydrochloride (0.94 g, 5.66 mmol) and Z-NMe-(S)-valine (15, 1.5 g, 5.66 mmol) in DME (40 mL) was treated with diethyl phosphorocyanidate (0.92 mL, 6 mmol) and triethylamine (1.59 mL, 11.32 mmol). The mixture was stirred under argon at 0° C. for 2 hours and then 6 hours at room temperature. Upon addition of water (100 mL) the product was extracted with EtOAc (3×100 mL). The combined extracts were successively washed with 5% hydrochloric acid (2×100 mL), water (100 mL), saturated NaHCO$_3$ solution (2×100 mL), water (100 mL), and dried. The solvent was removed under reduced pressure and dipeptide (6) crystallized as needles from toluene-hexane (1.65 g, 77%); mp 104°–105C.; $[\alpha]^{30}_D$ −144° c=0.2, CHCl$_3$); EIMS (m/z) 376 (M$^{+b \cdot 8}$%), 220 (30), 176 (53), 128 (10), 91 (100); IR (NaCl) V$_{max}$ 2961, 1748, 1697, 1649, 1437, 1396, 1304, 1197, 1176, 1164 cm$^{-1}$H-NMR (300 MHz) δ, two major conformers in the ratio of 1:3: 0.85, 0.87 (d, J=6.6 Hz, 3H, Val CH$_3$) , 0.93, 0.99 (d, J=6.5 Hz, 3H, Val CH$_3$) , 1.80–2.04, 2.17–2.23 (m, 4H, 2 × Pro CH$_2$), 2.26 (m, 1H, Val CHβ) , 2.92, 2.94 (s, 3H, N-CH$_3$), 3.67–3.73 (m, 1H, 0.5 Pro CH$_2$), 3.68, 3.72 (s, 3H, OCH$_3$), 3.89 dt, J=10, 6.8 Hz, 1H, Pro CHα), 4.36, 4.62 (d, J=11 Hz, 1H, Val CHα), 4.43 (dd, J=8.6, 3.8 Hz, Pro CHα). 5.03≅5.28 (m, 2H, benzyl CH$_2$), 7.27–7.36 (m, 5H, phenyl); $^{13}$C-NMR (400 MHz): 18.60 (Val CH$_3$), 18.79 (Val CH$_3$), 24.84 (Pro CH$_2$), 27.58 (Val CH), 27.59 (Pro CH$_2$), 29.12 (N-CH$_3$), 47.25 (Pro CH$_2$), 52.02 (Pro CH), 58.85 (Val CH), 61.79 (Pro OCH$_3$), 67.26 (ARCH$_2$O), 127.53, 127.89, 128.46 (ARCH), 136.60 (Val CO), 157.11, 169.72 (Val CO), 172.49 (Pro CO).

Anal. Calcd for C$_{20}$H$_{28}$N$_2$O$_5$: C, 63.81; H, 7.50; N, 7.44. Found: C.63.79; H, 7.48; N, 7.47.

Z-(S)-Val-NMe-(S)-Val-(S)-Pro-OMe (7)

A mixture of dipeptide (6) (1.15 g, 3.05 mmol) in EtOAc-methanol (3:1) and 10% palladium/carbon (0.20 g) was vigorously stirred in a hydrogen atmosphere for 4 hours. The solution was filtered and the filtrate concentrated to the clear, oily amine. Pivaloyl chloride (0.75 mL, 6.12 mmol) and N-methylmorpholine (1.34 mL, 12.24 mmol) were added to a vigorously stirred and cooled (–23° C.) solution of Z-(S)-valine (1.54 g, 6.12 mmol) in CH$_2$Cl$_2$ (20 mL). The solution was stirred (under argon) for 3 hours at the same temperature and the dipeptide (6) hydrogenation product was added. After stirring at –23° C. for 4 hours and at room temperature for 24 hours, CH$_2$Cl$_2$ (100 mL) was added. The solution was washed with saturated citric acid (3×40 mL), water (20 mL), saturated NaHCO$_3$ solution (2×40 mL), and finally water (40 mL). After drying and concentrating, the clear oil was dissolved in CH$_2$Cl$_2$ (10 mL) and applied to a column of SILICA GEL. Upon eluting with CH$_2$Cl$_2$-EtOAc (4:1) corresponding fractions were combined and concentrated to yield tripeptide (7) (1.2 g, 83%) as a colorless glass; [α]$^{30}_D$ –145° (c=0.26, CHCl$_3$); EIMS (m/z): 475 M$^+$, 5%, 444 (2), 346 (12), 206 (14), 162 (20), 91 (100); IR (NaCl) V$_{max}$ 3300, 2963, 17.49, 1720, 1637, 1437, 1260, 1234, 1216, 1198, 1176 cm$^{-1}$ NMR (300 MHz) δ 0.75 (d, J=6.6 Hz, 3H, Val CH$_3$), 0.86 (d, J=6.6 Hz, 3H, NMe-Val CH$_3$), 0.91 (d, J=6.6 Hz, 3H, Val CH$_3$), 1.81–2.04 (m, 4H, Pro 2 × CH$_2$), 2.17 (m, 1H, Val CHβ), 2.28 (m, 1H, NMe-Val CHβ), 3.21 (s,3H,N-CH$_3$) 3.66 (m, 1H, Pro 0.5 CH$_2$), 3.70 (s, 3H, Pro OCH$_3$), 3.91 (m, 1H, Pro 0.5 CH$_2$), 4.37 (dd, J=8.2, 5.7 Hz, 1H, Pro CHα), 4.49 (dd, J=9.2, 6.4 Hz, 1H, Val CHα), 5.04 (d, J=11.2 Hz, 1H, NMe-Val CHα), 5.07 (s, 2H, benzyl CH$_2$), 5.46 (d, J=9.2 Hz, 1H, Val NH), 7.31 (m, 5H, phenyl); $^{13}$C NMR (400 MHz): 17.31, 19.39, (Val CH$_3$'s) , 18.55, 18.80 (NMe-Val CH$_3$'s), 25.01, 29.22, 47.37 (Pro CH$_2$'s), 27.29 (NMe-Val CH), 30.57 (N-CH$_3$), 31.05 (Val CH) , 52.12 (Pro CHα), 56.05 (Val CH), 58.85 (NMe-Val CH), 59.27 (Pro OCH3), 66.85 (ArCH$_2$O), 127.90, 128.07, 128.48, 136.41 (Val ArC's), 156.39, 173.11 (Val CO's), 169.40 (NMe-Val CO), 172.43 (Pro CO).

Anal. Calcd for C$_{25}$H$_{37}$N$_3$O$_6$: C, 63.14; H, 7.86; N, 8.84. Found: C, 63.05; H, 8.04; N, 8.77.

Z-(S)-Val-NMe-(S)-Val-(S)-pro (8)

The Z-tripeptide (7) (0.95 g, 2 mmol) was stirred for 2 hours in a solution of 1N sodium hydroxide (3 mL, 3 mmol), water (10 mL), and ethanol (10 mL). The clear solution was concentrated to half its volume and acidified to pH 3.0 using 1N hydrochloric acid. The organic material was extracted using EtOAc (3×25 mL) and the combined extracts were washed with water (50 mL), dried and concentrated to a clear glass (0.92 g, 100%): [α]$^{23}_D$ –145° (c=0.26, CHCl$_3$); $^1$H NMR (300 MHz) δ0.83–0.98 (m, 12H, 4 × Val CH$_3$), 1.87–2.08 (m, 4H, 2 × Pro CH$_2$), 2.32 (m, 2H, 2 × Val CHβ), 3.15 (s, 3H, N-CH$_3$), 3.67 (m, 1H, 0.5 Pro CH$_2$), 3.91 (m, 1H, 0.5 Pro CH$_2$) , 4.52 (m, 1H, Pro CHα), 5.08 (d, J=11.1 Hz, 1H, NMe-Val CHα), 5.09 (s, 2H, Phe CH$_2$), 5.58 (d, J=9.4 Hz, 1H, NH), 7.35 (s, 5H, phenyl), carboxylic acid not seen: $^{13}$C NMR (400 MHz), 17.51, 18.32, 18.67, 9.14, 24.74, 27.16, 28.76, 30.85, 47.37, 56.17, 58.82, 59.32, 6.66, 127.66, 127.74, 127.85, 128.29, 136.36, 156.45, 169.58, 73.75 and 174.78.

Z-(S)-Val-NMe-(S)-Val-(S)-Pro-(S)-Pro-(S-Hiva-(S)-Dpy (9a)

To a cooled (0°) and stirred solution of tripeptide (8) (0.39 g, 0.97 mmol), depsipeptide (5b) (0.46 g,1 mmol) and triethylamine (0.27 mL, 2 mmol) in CH$_2$Cl$_2$ (25 mL) was slowly added diethyl phosphorocyanidate (0.167 mL, 1.1 mmol). The dry solution was stirred for 18 hours, concentrated to an oil, dissolved in CH$_2$Cl$_2$ (5 mL) and applied to a column of SILICA GEL. Elution with 5% ethanol in CH$_2$Cl$_2$ solution led to a clear glass (0.73 g, 89%) [α]$^{23}_D$ –65° (C=0.26, CHCl$_3$); FAB MS m/z): 984 [M+H$^+$]. $^1$H-NMR (300 MHZ) δ0.82–0.94 (m, 12H, 4 × Val CHβ), 3.05 (dd, J=14.0, 3.5, Hz, 1H, 0.5 Phe CH$_2$), 3.16 (s, 3H, N-CH$_3$), 3.54 (dd, J=14.0, 4.3 Hz, 1H, 0.5 Phe CH$_2$), 3.60 (m, 1H, 0.5 Pro CH2), 3.76 (s, 3H, OCH$_3$), 3.77 (m, 2H, Pro CH$_2$), 3.92 (m, 1H, 0.5 Pro CH$_2$), 4.53 (m, 1H, CHα), 4.64 (m, 1H, CHα), 4.73 (s, 1H, H-3), 4.78 (m, 1H, H-5), 4.85 (dd, J=8.6, 2.5 Hz, 1H, CHα), 5.08 (m, 1H, NMe-Val CHα), 5.10 (s, 2H, Z-Val CH$_2$), 5.46 (bd, J=9.5 Hz, 1H, NH), 5.90 (d, J=2.7 Hz, 1H, Hiva CHα), 7.14–7.24 (m, 5H, phenyl), 7.35 (s, 5H, 5 × Z-Val phenyl); $^{13}$C NMR (400 MHz): 15.80, 17.30, 18.65, 19.18, 19.47, 19.81, 24,61, 24.69, 27.46, 28.36, 28.53, 28.87, 30.66, 31.17, 34.88, 46.37, 47.77, 56.04, 58.08, 58.30, 59.39, 59.87, 66.85, 77.84, 94.73, 126.98, 127.90, 128.12, 128.49, 129.98, 134.175, 136.45, 156.42, 169.24, 169.24, 169.47, 170.18, 171.44, 172.95, 178.18.

Anal. Calcd for C$_{46}$H$_{61}$N$_5$O$_{10}$: C, 65.46; H, 7.29; N, 8.30. Found: C, 64.80 H, 7.32; N, 8.22.

(S)-Val-NMe-(S)-Val-(S)-Pro-(S)-Pro-(S)-Hiva-(S) -Dpy (9b)

A mixture of the Z-peptide (9a, 0.83 g, 0.986 mmol) and 10% pd/C (0.8 g) was stirred vigorously in EtOAc (20 mL) under a hydrogen atmosphere (balloon pressure) for 18 hours. After filtration, the clear solution was concentrated, the residue dissolved in CH$_2$Cl$_2$ (5 mL), added to a column of SILICA GEL and the product eluted with 5% ethanol in CH$_2$Cl$_2$ to afford a clear glass (0.655 g, 96%); [α]$^{24}_D$ –49.6° (c=0.26, CHCl$_3$); $^1$H-NMR (300 MHz) δ 0.87– 0.98 (m, 12H, 4 × Val CH$_3$), 1.06–1.09 (m, 6H, 2 x Val CH$_3$), 1.87–2.44 (m, 11H, 4 × Pro CH$_2$, 3 × Val CHβ) , 3.06 (dd, J=14.2, 3.5 Hz, 1H, 0.5 Phe ArCH$_2$), 3.09 (s, 3H, N-CH$_3$), 3.53 (dd, J=14.2, 4.4 Hz, 1H, 0.5 Phe CH$_2$), 3.62 (m, 1H, 0.5 Pro CH$_2$), 3.76 (s, 3H, OCH$_3$), 3.77 (m, 2H, Pro CH$_2$), 3.85 (m, 1H, 0.5 Pro CH$_2$), 4.64 (m, 1H, CHα), 4.72 (s, 1H, H-3), 4.78 (t, J=3.9 Hz, 1H, H-5), 4.85 (dd, J=8.6, 2.6 Hz, 1H, CHα)m 4,96 (m, 1H, CHα), 5.16 (d, J=11.1 Hz, 1H, NMe-Val CHα) , 5.90 (d, J=2.7 Hz, 1H, Hiva CHα) , 7.14–7.23 (m, 5H, phenyl); $^{13}$C-NMR (400 MHz: 15.80, 16.70, 18.82, 19.26, 19.86, 20.00, 24/63, 24.73, 27.50, 28.39, 28.86, 30.38, 31.72, 34.87, 46.38, 47.80, 56.68, 58.10, 58.27, 58.34, 59.33, 59.87, 77.86, 94.76, 127.01, 128.15, 130.00, 134.16, 169.30, 169.50, 170.26, 171.46, 178.20.

Anal. Calcd for C$_{38}$H$_{55}$N$_5$O$_8$: 1.5 H$_2$O; C. 63.67, H, 8.16; N, 9.77. Found: C, 63.49; H, 7.94; N. 9.67.

(S)-Dov-(S)-Val-(S)-NMe-Val-(S)-Pro-(S)-Pro-(8)-Hiva-(S)-Dpy (Dolastatin 15, 1). To a cooled (0°) and stirred solution (dry) of (9b) (3.85 g, 5.58 mmol), dimethylvaline (Dov, 0.99 g, 6.8 mmol), and triethylamine (0.97 mL, 6.8 retool) in $CH_2Cl_2$ (100 mL) was slowly added diethyl phosphorocyanidate (1.02 mL, 6.8 mmol). After 2 hours the clear solution was concentrated, dissolved in $CH_2Cl_2$ (15 mL), applied to a column of SILICA GEL and the dolastatin 15 eluted with 5% ethanol in $CH_2Cl_2$ to provide a clear glass (4.54 g, 97%) which was identical (see above) to natural (−)-dolastatin 15. In some cases further purification of dolastatin 15 was required and achieved by applying 500 mg aliquots in 5 mL of hexane-acetone (1: 1) to a LOBAR pre-packed column (Size B, Si 60) and eluting with hexane-acetone (1:1) at 10 psi. The appropriate fractions were collected and concentrated under reduced pressure. With less tenacious impurities rapid gel permeation chromatography in methanol on a column of SEPHADEX LH-20 proved useful. Recrystallization from toluene-hexane afforded analytically pure dolastatin 15 (1) as colorless crystals: mp 175°–175.5° C.; HPTLC-$SiO_2$ plate, Hexane: acetone-2:3, $R_f$=0.31; HPLC-PHENOMENEX ULTRAMEX 3 $C_8$ column (100 cm × 4.6 mm), $R_t$ 3.8 min, MeOH:buffer(0.05M $KH_2PO_4$)- 3:1, flow rate 1 ml/min; $[\alpha]^{24}_D$ −77° (c=0.2, $CH_3OH$); UV (in $CH_3OH$) ($\epsilon$) $\lambda_{max}$ 208nm (49,700), 240nm (19,500); FAB MS (m/z): 838 (13.7, M+H$^+$), 498 (100); 340 (93.6)%; IR (KBr) 3587, 3383, 2964, 2876, 1732, 1631, 1446, 1307, 1186, cm$^{-1}$ $^1$H-NMR (300 MHz) δ 0.78 (t, J=6.6 Hz, 3H, Val $CH_3$), 0.92–0.95 (m, 12H, 4 × Val $CH_3$), 0.99– 1.09 (m, 9H, 3 × Val $CH_3$), 1.82–2.45 (m, 12H, 4 × Pro $CH_2$, 4 × CHβ), 2.26 (s, 6H, 2 × $CH_3$, 2.46 (bd, J=6.1 Hz, 1H, Dov CHα), 3.04 (dd, J=14.0, 3.5 Hz, 1H, 0.5 Phe $CH_2$). 3.18 (s, 3H, N-$CH_3$), 3.54 (dd, J=14.0, 4.5 Hz, 0.5 Phe $CH_2$), 3.61 (m, 1H, 0.5 Pro $CH_2$), 3.76 (s, 3H, $OCH_3$), 3.77 (m, 2H, Pro $CH_2$), 3.80 (m, 1H, 0.5 Pro $CH_2$), 4.65 (m, 1H, CHα), 4.73 (s, 1H, H3) 4.79 (m, 2H, 2 × CHα), 4.84 (dd, J=8.7, 2.7 Hz, 1H, H-5), 1H, H-5), 5.14 (d, J=11.1 Hz, NMe-Val CHα), 5.90 (d, J=2.6 Hz, 1H, Hiva CHα) , 6.92 (bd, J=8.9 Hz, 1H, NH), 7.14–7.23 (m, 5H, phenyl); $^{13}$C NMR (400 MHz): 15.76, 17.61, 18.08, 18.51, 19.13, 19.55, 19.81, 20.16, 24.66, 27.27, 27.65, 28.35, 28.52, 28.83, 30.67, 31.08, 34.84, 42.94, 46.35, 47.79, 53.61, 58.03, 58.23, 59.16, 59.83, 77.82, 94.71, 125.27, 126.96, 128.11, 128.20, 129.00, 129.96, 134.15, 169.10, 169.25, 169.45, 170.18, 171.43, 171.78, 172.95, 178.16.

Anal. Calcd for $C_{45}H_{68}N_6O_9$: C, 64.57; H, 8.19; N, 10.04. Found: C, 64.16; H, 7.99; N, 9.82.

In order to unequivocally establish the absolute configuration of depsipeptide (5a), a specimen crystallized from acetone-hexane was subjected to X-ray crystal structure analysis. A crystal of depsipeptide (5a) with dimensions ≈0.40×0.40×0.30 mm was obtained by cleavage from a larger specimen; Crystal data: intermediate 7, $C_{27}H_{36}N_2O_7$, orthorhombic, space group $P2_12_12_1$, with a=10.9247(10), b=12.8687(24), c=20.358(24) Å, α=β=V=90°, V=2816.77 Å, $\rho_o$=1.160 g cm$^{-3}$, $\rho_o$=1.181 g cm$^{-3}$ for Z=4. Data was collected to a maximum of 2θ=150° on an ENRAF-NONIUS CAD-4 diffractometer at 26°± 1° C. The ω/2θ scan technique was used with graphite monochromated Cu Kα radiation (λ1.5418 Å). After measurement of each reflection, the FRIEDEL equivalent was also collected (whenever possible). After Lorentz and polarization corrections, merging of equivalent reflections and rejection of systematic absences, a total of 3907 reflections (Fo >5σ(Fo)) were used in the structure determination. An empirical absorption correction was made using the psi scan technique described by Watkin et al. in the 1985 *Crystals User Guide*, V. of Oxford, Eng. Direct methods (SHELXS-86) were used in the structure determination. Refinement was performed with CRYSTALS-86. A weighing scheme was used in which: (W=[weight] * [1-( F/6*$\sigma_F$)$^2$]$^2$), where [weight] is determined by a Chebyshev series of $F_c$/Fo(max). The hydrogen atom coordinates were calculated at optimum positions and were included but not refined in the final cycle of least-squares refinement. Full matrix least-squares anisotropic refinement on all nonhydrogen atoms, and isotropic temperature factors (U=0.06) for hydrogens yielded standard crystallographic residuals of R=0.061, Rw=0.076. Absolute stereochemical assignments to the three chiral centers was made, based upon the known stereochemical configuration of S-Pro. The stereochemical designations for the three chiral centers were determined to be C-4(S), C-7(S) and C-10(S).

SCHEME 1

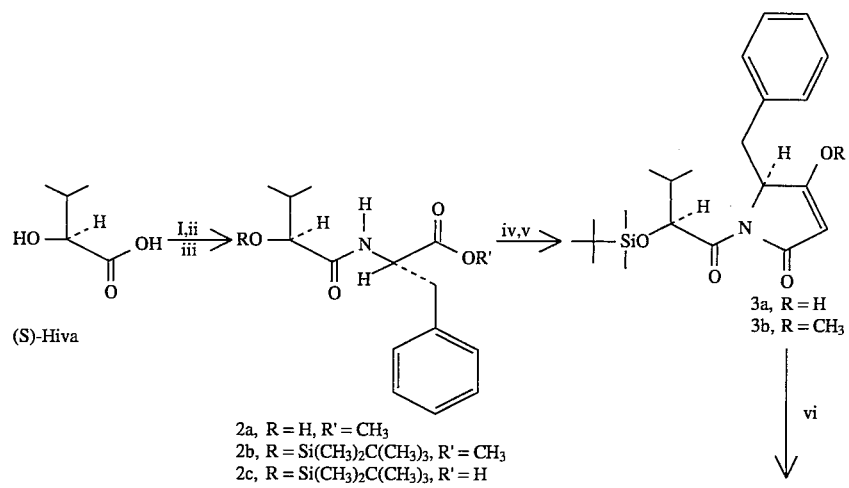

2a, R = H, R' = $CH_3$
2b, R = Si($CH_3$)$_2$C($CH_3$)$_3$, R' = $CH_3$
2c, R = Si($CH_3$)$_2$C($CH_3$)$_3$, R' = H

3a, R = H
3b, R = $CH_3$

-continued
SCHEME 1

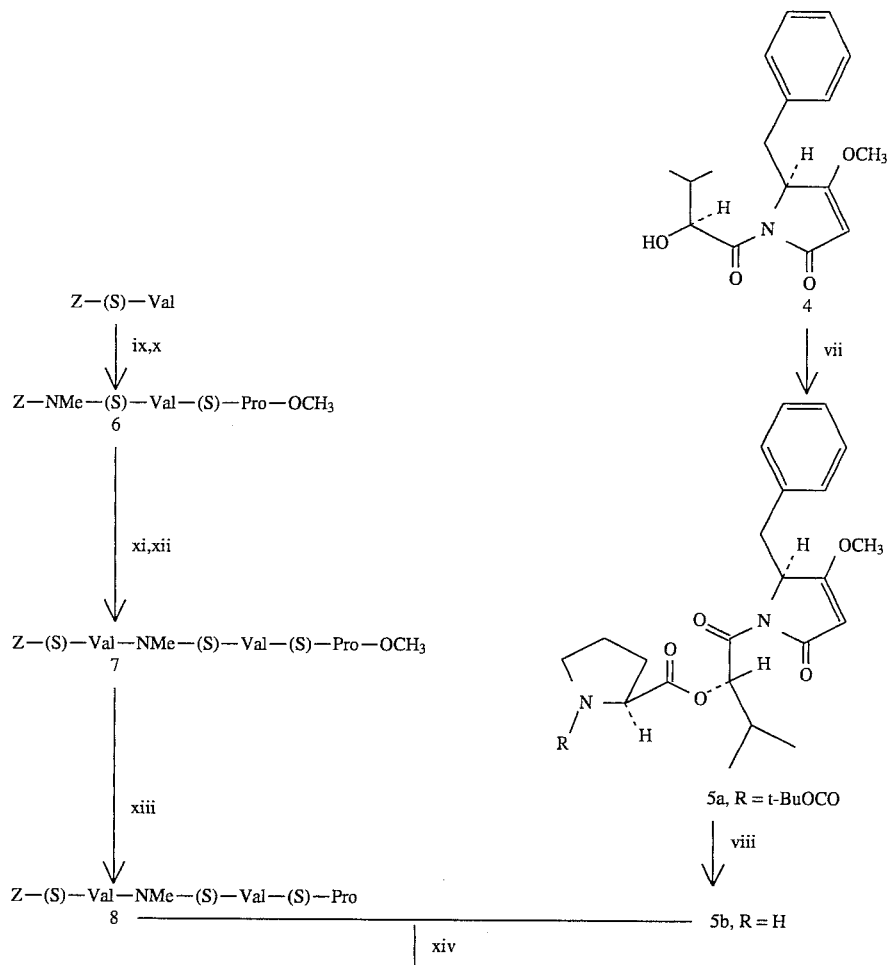

Dolastatin 15

(i) Phe—OMe.HCl, diethyl phosphorocyanidate (DEPC), NMM, $CH_2Cl_2$;
(ii) TBDMS chloride, imidazole, DMF;
(iii) 1 N NaOH, $CH_3CH_2OH-H_2O$;
(iv) Meldrum's ester, 4-DMAP, $ClCO_2C(CH_3)=CH_2$, $CH_2Cl_2$; toluene, Δ;
(v) $K_2CO_3$, $(CH_3O)_2SO_2$, THF;
(vi) TFA;
(vii) Boc—(S)—Pro, DCCI, 4-pyrrolidinopyridine, $CH_2Cl_2$;
(viii) TFA, $CH_2Cl_2$;
(ix) NaH, $CH_3I$, THF;
(x) S—Pro—$OCH_3$.HCl, DEPC, TEA, DME;
(xi) $H_2$, 10% Pd/C, EtOAc—$CH_3OH$;
(xii) Z—(S)—Val, $(CH_3)_3CCOCl$, NMM, $CH_2Cl_2$;
(xiii) 1 N NaOH, $CH_3OH-H_2O$;
(xiv) DEPC, TEA, $CH_2Cl_2$, 0° C.;
(xv) $H_2$, 10% Pd/C, ETOAc—$CH_3OH$;
(xvi) (S)—Dov, DEPC, TEA, $CH_2Cl_2$, 0° C.

From the foregoing, it is readily apparent that a useful embodiment of the present invention has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

Accordingly, what is claimed is:

1. A method of synthesizing dolastatin 15 comprising the steps of:

coupling tripeptide (8) and tripeptide (5b) to form peptide (9a);

hydrogenating said peptide (9a) to form peptide (9b);

coupling said peptide (9b) with Dov to form dolastatin 15; and isolating said dolastatin 15.

2. The method according to claim 1, further including the step of:

purifying said dolastatin 15.

3. The method according to claim 1, wherein said step of coupling tripeptide (8) and tripeptide (5b) involves using DEPC to couple said tripeptide (8) and tripeptide (5b).

4. The method according to claim 3, further including the step of:

purifying said dolastatin 15.

5. The method according to claim 1, wherein said tripeptide (8) is produced by:

coupling Z-NMe-(S)-Val with (S)-Pro-OMe to form dipeptide (6);

hydrogenating said dipeptide (6) followed by coupling with Z-(S)-Val to form tripeptide (7); and removing said methyl ester group from said tripeptide (7) to form said tripeptide (8).

6. The method according to claim 5, wherein said step of coupling tripeptide (8) and tripeptide (5b) involves using DEPC to couple said tripeptide (8) and tripeptide (5b).

7. The method according to claim 6, further including the step of:

purifying said dolastatin 15.

8. The method according to claim 1, wherein said tripeptide (5b) is produced by:

diazotating S-valine to form S-(Hiva);

coupling said S-(Hiva) with Phe-OMe to form (2a);

protecting said (2a) as silyl ether (2b);

saponifying said (2b) to form (2c);

cyclizing said (2c) to form (3a);

methylating said (3a) to form (3b);

removing the silyl group from said (3b) to form alcohol (4);

esterifying said alcohol (4) to form (5a) having a Boc-protecting group; and removing said Boc-protecting group from said (5a) to form said (5b).

9. The method according to claim 8, wherein said step of coupling tripeptide (8) and tripeptide (5b) involves using DEPC to couple said tripeptide (8) and tripeptide (5b).

10. The method according to claim 9, further including the step of:

purifying said dolastatin 15.

11. The method according to claim 8, wherein said tripeptide (8) is produced by:

coupling Z-NMe-(S)-Val with (S)-Pro-OMe to form dipeptide (6);

hydrogenating said dipeptide (6) followed by coupling with Z-(S)-Val to form tripeptide (7); and removing said methyl ester group from said tripeptide (7) to form said tripeptide (8).

12. The method according to claim 11, wherein said step of coupling tripeptide (8) and tripeptide (5b) involves using DEPC to couple said tripeptide (8) and tripeptide (5b).

13. The method according to claim 12, further including the step of:

purifying said dolastatin 15.

14. A method of synthesizing dolastatin 15 comprising the steps of:

a) coupling tripeptide (8) and peptide (5b) with diethylphosphorocyanidate (DEPC) to form peptide (9a), b) deprotecting peptide (9a) by hydrogenolysis to form peptide (9b), c) coupling peptide (9b) and Dov with DEPC to form dolastatin 15, and d) isolating said dolastatin 15.

15. The method according to claim 14 in which said tripeptide (8) is produced by condensing N-Z (wherein Z is a carbobenzoxy protecting group), N-Me-(S)-Val and (S)-Pro-Me with DEPC to form dipeptide (6), cleaving the carbobenzoxy protecting group by hydrogenolysis to produce deprotected dipeptide (6), and coupling the deprotected peptide with mixed anhydride prepared from pivaloyl chloride and Z-(S)Val.

16. The method according to claim 14 in which said isolated dolastatin 15 is subsequently purified on a SEPHADEX LH-20 chromatography column.

17. The method according to claim 14 in which said depsipeptide comprises an amorphous powder having a melting point of about 175°–175.5° C., $[\alpha]_D^{24}$ –77° (C, 0.2, $CH_3OH$).

18. The method according to claim 14 in which said depsipeptide, when identified by TLC, $^1H$ and $^{13}C$-NMR is identical to natural (−)- dolastatin 15.

19. The method of claim 14 in which said peptide (5b) is produced by coupling S-Hiva and Phe-OMe hydrochloride with diethyl phosphorocyanidate to form (S)-Hiva-(S)-Phe-OMe (2a); reacting said (S)-Hiva-(S)-Phe-OMe (2a) with t-butyldimethylsilyl chloride; cleaving the methyl ester under mild alkaline conditions (2a→2c); deriving dolapyrolidone (3a) from (2c) and isopropenyl chloroformate in the presence of 4-methylamino-pyridine; methylating dolapyrolidone (3a) with dimethylsulfate to produce silyl ether (3b); cleaving the silyl ether (3b), using trifluoroacetic acid, to alcohol (4); esterifying alcohol (4) with Boc-(S)-Pro using dicyclohexylcarbodiimide to produce depsipeptide (5a); and converting depsipeptide (5a) with trifluoroacetic acid to form tripeptide (5b).

\* \* \* \* \*